(12) United States Patent
Cross, III

(10) Patent No.: US 12,329,818 B2
(45) Date of Patent: Jun. 17, 2025

(54) TOPICAL COMPOSITIONS AND METHODS FOR TREATMENT OF DIABETIC NEUROPATHIES

(71) Applicant: William H. Cross, III, Waco, GA (US)

(72) Inventor: William H. Cross, III, Waco, GA (US)

( * ) Notice: Subject to any disclaimer, the term of this patent is extended or adjusted under 35 U.S.C. 154(b) by 0 days.

(21) Appl. No.: 16/283,660

(22) Filed: Feb. 22, 2019

(65) Prior Publication Data

US 2019/0275154 A1 Sep. 12, 2019

Related U.S. Application Data

(60) Provisional application No. 62/634,166, filed on Feb. 22, 2018.

(51) Int. Cl.
| | |
|---|---|
| *A61K 47/20* | (2006.01) |
| *A61K 9/00* | (2006.01) |
| *A61K 31/122* | (2006.01) |
| *A61K 31/197* | (2006.01) |
| *A61K 31/205* | (2006.01) |
| *A61K 31/4166* | (2006.01) |
| *A61K 31/4415* | (2006.01) |
| *A61K 31/522* | (2006.01) |
| *A61K 31/593* | (2006.01) |
| *A61K 47/42* | (2017.01) |
| *A61P 29/02* | (2006.01) |

(52) U.S. Cl.
CPC ............ *A61K 47/20* (2013.01); *A61K 9/0014* (2013.01); *A61K 31/122* (2013.01); *A61K 31/197* (2013.01); *A61K 31/205* (2013.01); *A61K 31/4166* (2013.01); *A61K 31/4415* (2013.01); *A61K 31/522* (2013.01); *A61K 31/593* (2013.01); *A61K 47/42* (2013.01); *A61P 29/02* (2018.01)

(58) Field of Classification Search
None
See application file for complete search history.

(56) References Cited

U.S. PATENT DOCUMENTS

| | | | | |
|---|---|---|---|---|
| 3,711,602 | A * | 1/1973 | Herschler | A61K 9/0014 424/45 |
| 5,719,119 | A | 2/1998 | Veech | |
| 7,060,295 | B2 | 6/2006 | Richardson | |
| 7,645,742 | B2 | 1/2010 | Stohs | |
| 9,414,615 | B2 | 8/2016 | Sridhar | |
| 10,945,979 | B1 | 3/2021 | Schroeder | |
| 2001/0011083 | A1 * | 8/2001 | Barr | A61K 36/752 514/159 |
| 2001/0031744 | A1 * | 10/2001 | Kosbab | A61K 36/9068 514/54 |
| 2005/0118261 | A1 * | 6/2005 | Oien | A61K 9/0014 424/468 |
| 2005/0129783 | A1 | 6/2005 | McCleary | |
| 2011/0313043 | A1 | 12/2011 | Kramer | |
| 2012/0232003 | A1 | 9/2012 | Takahashi | |
| 2013/0052271 | A1 * | 2/2013 | Sternasty | A61K 9/4875 514/35 |
| 2014/0044685 | A1 | 2/2014 | Greenberg | |
| 2016/0228409 | A1 * | 8/2016 | Cross, III | A61K 31/185 |
| 2017/0312329 | A1 | 11/2017 | Cross, III | |

FOREIGN PATENT DOCUMENTS

| | | | |
|---|---|---|---|
| CN | 101716182 | 4/2013 | |
| IN | 1306CHE2007 | 1/2009 | |
| WO | 2008048045 | 4/2008 | |
| WO | WO-2008048045 A1 * | 4/2008 | ................ A61P 9/00 |
| WO | 2013108262 | 7/2013 | |

OTHER PUBLICATIONS

Vita Sciences, Nervex Neuropathy Pain Relief, Jan. 26, 2017 (Year: 2017).*
Till Wagner, Capsaicin 8% patch for peripheral neuropathic pain: review of treatment best practice from real world clinical experience, 2012, Pain Management, Future Science Group, vol. 2, No. 3, 239-250 (Year: 2012).*
Martina Hagen & Mark Baker, Skin penetration and tissue permeation after topical administration of diclofenac, 2017, Current Medical Research and Opinion, 33:9, 1623-1634, DOI: 10.1080/03007995.2017.1352497 (Year: 2017).*
Colin Tidy, Peripheral Neuropathy, Jul. 30, 2017, Patient.info (Year: 2017).*
Bell, D.S.H., 2012, Case Report in Endocrinology, Article ID 165056, 3pp.
Curtis, L., 2013, International Journal of Diabetes Research, 2:56-60.
Hagen, M. et al., 2017, Current Medical Research and Opinion, 33(9):1623-1634.
Henriksen, E.J., 2006, Free Radical Biology & Medicine, 40:3-12.
Lautt et al., 2010, Can. J. Physiol. Pharmacol., 88:313-323.
Shinohara, T. et al., 2004, J. Biol. Chem., 279:23559-23564.
VITA Sciences, Nervex Neuropathy Pain Relief (Product Literature), Jan. 26, 2017.
Wagner, T., 2012, Pain Management, 2(3):239-250.
Wojtczak, A., 2002, Medical Teacher, 24:658-660.
Yonguc, et al., 2015, Gene, 555:119-126.
McCarty, M.F., 2017, Healthare, 5, 28pp (doi:10.3390/healthcare5010015).

(Continued)

*Primary Examiner* — Scarlett Y Goon
*Assistant Examiner* — Ali S Saeed
(74) *Attorney, Agent, or Firm* — Thomas | Horstemeyer, LLP

(57) ABSTRACT

The invention provides topical compositions and methods to treat diabetic neuropathies. Compositions of the invention comprise: aqueous solvent mixtures; natural polyamides comprising large amounts of small amino acid residues; compounds characteristic of biosynthesis and metabolism of L-carnitine, carnosine, vitamin D3, vitamin B5 and vitamin B6; purines and their decomposition compounds; and coenzyme Q10.

18 Claims, No Drawings

(56) References Cited

OTHER PUBLICATIONS

U.S. Appl. No. 15/017,527, 20160228409, filed Aug. 11, 2016.
U.S. Appl. No. 15/496,919, 20180303896, filed Oct. 25, 2018.
U.S. Appl. No. 15/650,825, 20170312329, filed Sep. 6, 2019.
U.S. Appl. No. 16/264,595, 20190231806, filed Aug. 1, 2019.
U.S. Appl. No. 16/264,609, 20190231807, filed Aug. 1, 2019.
U.S. Appl. No. 16/264,614, 20190231725, filed Aug. 1, 2019.
U.S. Appl. No. 17/352,674.
U.S. Appl. No. 15/017,527, filed Aug. 11, 2016.
U.S. Appl. No. 15/496,919, filed Oct. 25, 2018.
U.S. Appl. No. 15/650,825, filed Sep. 6, 2019.
U.S. Appl. No. 16/264,595, filed Aug. 1, 2019.
U.S. Appl. No. 16/264,609, filed Aug. 1, 2019.
U.S. Appl. No. 16/264,614, filed Aug. 1, 2019.

* cited by examiner

TOPICAL COMPOSITIONS AND METHODS FOR TREATMENT OF DIABETIC NEUROPATHIES

CROSS-REFERENCE TO RELATED APPLICATIONS

This application derives priority from provisional application U.S. Ser. No. 62/634,166, filed Feb. 22, 2018 and having the same title and sole inventor.

FIELD OF THE INVENTION

The invention concerns compositions and methods for the treatment and prevention of diabetic neuropathies.

BACKGROUND

Diabetes mellitus is a carbohydrate metabolism disorder caused by insufficient insulin production and or reduced sensitivity to insulin. Consequently, the cells are inhibited from normal glucose utilization, resulting in abnormally high blood sugar levels and a variety of maladies.

Chronic complications include diabetic retinopathy (retinal changes leading to blindness), kidney disease and frequent infection. Acute complications from diabetes may be fatal, such as "dead-in-bed syndrome" and such as "diabetic shock" wherein a diabetic person suddenly and without warning becomes temporarily blind, disoriented and or loses consciousness during normal activity. To date there is no cure for diabetes.

Diabetes is the leading known cause for development of neuropathy in developed countries. And in fact, diabetic neuropathy affects almost 2% of the global population and about 20% of the diabetic population, and is the leading cause of morbidity and mortality in diabetes patients. It is believed to be responsible for between 50% and 75% of nontraumatic amputations. Hyperglycemia is the main risk factor, but with treatment the incidence of diabetic neuropathy is lowered almost four-fold in Type 1 diabetic patients. Other factors include the patient's age, smoking, hypertension, height and hyperlipidemia, and length of personal history with diabetes.

At an early stage diabetic neuropathies are typically associated with microvascular injuries in which blood cells supplying nerves narrow and then capillary membranes thicken, reducing the oxygen supply to nerves and resulting in ischemia of neurons. For that reason, agents that dilate blood vessels are often administered. Several other pathologies contribute. Irregularities in the polyols pathway may also contribute to microvascular damage. High glucose levels within cells also lead to non-enzymatic glycosylation of proteins, which causes inhibition of their function.

Polyneuropathies manifest in various ways. Sensorimotor polyneuropathy affects longer nerve fibers more, and reduces sensation and reflexes, appearing in the extremities first as numbness and night-time pain which may burn, ache or feel prickly.

Autonomic neuropathy affects several organ systems such as the heart, lungs, blood vessels, bones, fatty tissue, sweat glands, gastrointestinal system and genitourinary system. A common form of the disorder leads to fainting upon standing up due to orthostatic hypotension, and is also associated with respiratory sinus arrhythmia. Where the disorder affects the gastrointestinal tract it can reduce absorption of oral diabetes medications, resulting in hypoglycemia, meanwhile reduced rate of movement through the intestines can lead to bacterial overgrowth and resulting bloat, gas and diarrhea in patients with high blood sugar. Reflux nephropathy is one result for urinary symptoms, together with other outcomes when urinary retention results from urinary tract infections.

Cranial neuropathies may affect the eye's oculomotor nerve (cranial nerve #3 associated with third nerve palsy) abruptly with frontal pain, and they may begin with the nerve fibers furthest from the vascular supply. This affects eyelid movement and pupil constriction. Neuropathies that affect the sixth nerve, i.e., the abducens nerve, affect lateral eye movement. In some cases the fourth (trochlear) nerve is affected, associated with downward eye movement. Mononeuropathies of certain spinal nerves mimic the symptoms of myocardial infarction, cholecystitis or appendicitis. And entrapment neuropathies in diabetics commonly lead to carpal tunnel syndrome.

Generally neuropathic symptoms develop over a period of years. Symptoms vary between the disorders: they range from weakness, imbalance and muscle contraction; to sexual dysfunctions; to vision changes and impaired speech; to numbness or various types of pain or other sensations; to loss of control over the bladder or bowels.

Apart from control of blood sugar levels, treatment typically has the objective of managing pain and minimizing symptoms. The treatments employed fall into the following categories: tricyclic antidepressants (TCAs) at usually low dosages (for short-term relief of pain); serotoninnorepineprine reuptake inhibitors (SNRIs); selective serotonin reuptake inhibitor; antiepileptic drugs (AEDs, for short-term relief of pain); erythropoietin; natural remedies (e.g., supplements with vitamin B1, vitamin B12, alpha lipoic acid, and L-arginine to control pain); classic analgesics (opioids and or NSAIDs in combination with other treatments); medical devices (infrared, e.g., 890 nm to act upon cytochrome C to release nitric oxide and trigger vasodilation); and physical therapy (such as painless electric current to relieve stiffness, muscle training for gait and posture, exercise to minimize spasms and atrophy, ultrasound, etc.).

The mechanistic aspects of diabetic neuropathy are poorly understood so treatment has focused on symptom reduction though the disease is progressive. Even that is in need of improved approaches because, for instance, numbness in feet results in unwitting injuries, ulceration from small infections, and amputations. The problem's importance is evident in that sixty percent of lower extremity amputations are for diabetes patients. Moreover, the drugs used to treat diabetic neuropathy have a number of side effects users would not experience in their absence, thus: 38% of the users for diabetic neuropathic pain experience dizziness; 13% experience blurry vision and difficulty with depth perception; 9% experience increased neuropathy, i.e., a worsening of the pain at issue; and 14% become infected.

Consequently, there is an ongoing need for compositions to treat and prevent diabetic neuropathies.

SUMMARY OF THE INVENTION

The invention provides topical compositions and methods to treat and prevent diabetic neuropathies.

In a particular embodiment the composition provides a topical composition for alleviation of pain from a diabetic neuropathy, wherein the composition comprises:
   a) a plurality of solvents comprising at least water, dimethylsulfoxide (DMSO) and methylsulfonylmethane (MSM) present in ratios relative to each other, wherein:
      i) the composition comprises at least 45 weight percent water;

ii) the composition comprises at least 10 weight percent DMSO; and
iii) the ratio of DMSO to MSM is respectively between 4:1 and 50:1 by weight, inclusive;
b) at least one natural polyamide selected from the group consisting of proteins and peptides, wherein:
  i) at least 70 mole percent of the amino acid residues in the natural polyamide are selected from the group of small amino acids consisting of: glycine, alanine, serine, aspartic acid, and threonine; and
  ii) at least 50 mole percent of the amino acid residues in the natural polyamide are selected from the group of small amino acids consisting of: glycine, alanine, and serine; and
c) at least one compound characteristic of L-carnitine biosynthesis, wherein the compound is selected from the group consisting of: lysine; 6-N-trimethyllysine; hydroxytrimethyllysine (HTML); 4-trimethylaminobutyraldehyde (TMABA); gamma-butyrobetaine; L-carnitine; and acetyl-L-carnitine;
d) at least one compound characteristic of carnosine biosynthesis, wherein the compound is selected from the group consisting of: cytosine; uracil; beta alanine; and carnosine;
e) at least one compound selected from the group consisting of vitamin D3 and vitamin D3 metabolites, wherein the group consists of: cholecalciferol; calcifediol; and calcitriol;
f) coenzyme Q10 (coQ10), wherein the coQ10 is present in one or more redox states selected from the group consisting of: fully oxidized (ubiquinone); half oxidized (ubisemiquinone); and fully reduced (ubiquinol);
g) at least two compounds that are selected from the group consisting of purine compounds and purine decomposition compounds, present in ratios relative to each other, wherein:
  i) at least one compound is a purine compound selected from the group consisting of purine, adenine, adenosine, guanine, guanosine, isoguanine, inosine, hypoxanthine, xanthine, theobromine, and caffeine;
  ii) at least one compound is a purine decomposition compound selected from the group consisting of uric acid and allantoin; and
  iii) the ratio of the sum of purine decomposition compound(s) to the sum of purine compound(s) is respectively between 10:1 and 100:1 by weight, inclusive;
h) at least two B vitamins present in ratios relative to each other, comprising:
  i) at least one vitamin B5 compound that is selected from the group consisting of vitamin B5, provitamin B5 and salts of vitamin B5;
  ii) at least one vitamin B6 compound that is selected from the group consisting of pyridoxine (PN); pyridoxine 5'-phosphate (P5P); pyridoxal (PL); pyridoxal 5'-phosphate (PLP); pyridoxamine (PM); pyridoxamine 5'-phosphate (PMP); 4-pyridoxic acid (PA), and pyritinol; and
  iii) the ratio of the sum of vitamin B5 compounds to the sum of vitamin B6 compounds is respectively between 1:30 and 30:1 by weight, inclusive; and
i) the topical composition comprises:
  i) 0.5 to 1.5 weight percent in the aggregate of the at least one natural polyamide;
  ii) 0.25 to 1.0 weight percent in the aggregate of the at least one compound characteristic of L-carnitine biosynthesis;
  iii) 0.15 to 2.0 weight percent in the aggregate of the at least one compound characteristic of carnosine biosynthesis present in a range of, inclusive;
  iv) 0.15 to 1.5 weight percent in the aggregate of the at least one compound selected from the group consisting of vitamin D3 and vitamin D3 metabolites;
  v) 0.25 to 1.5 weight percent in the aggregate of the coQ10 that is present in one or more redox states;
  vi) 0.15 to 0.75 weight percent in the aggregate of the at least one purine decomposition compound(s);
  vii) 0.0025 to 0.25 weight percent in the aggregate of the at least one purine compound(s);
  viii) 0.05 to 5.0 weight percent in the aggregate of the at least one B5 compound(s); and
  ix) 0.05 to 5.0 weight percent in the aggregate of the at least one vitamin B6 compound(s).

wherein topical administration of a pharmaceutically effective amount of the composition is effective to alleviate diabetic neuropathic pain by a measure selected from the group consisting of: reducing that pain by at least 50% within 7 days after the onset of administration; and virtually eliminating that pain when the administration continues over a period of at least one month.

In a further embodiment, the invention provides a method for alleviating pain from a diabetic neuropathy by topical administration of a pharmaceutically effective amount of such a composition to a patient in need thereof.

DETAILED DESCRIPTION OF THE INVENTION

The invention may be further understood by consideration of the following definitions for the terms as used herein.

The term "diabetic" refers to the metabolic disorder diabetes mellitus and or its symptoms, and has its usual and ordinary meaning in the medicinal arts. The term includes each of the known types of diabetes including the classically defined categories of gestational diabetes, type 1 diabetes (from birth), and type 2 diabetes (later onset). The term "diabetic" further includes the five more recently classified genetically distinct groupings of patients, as follows. Cluster 1, currently known as type 1, pertains to severe autoimmune diabetes; it is characterized by insulin deficiency and the presence of autoantibodies; it has been identified in 6-15 percent of subjects. Cluster 2 pertains to severe insulin-deficient diabetes; it is characterized by younger age, insulin deficiency, and poor metabolic control, but no autoantibodies; it has been identified in 9-20 percent of subjects. Cluster 3 pertains to severe insulin-resistant diabetes; it is associated with a significantly higher risk of kidney disease and was identified in 11-17 percent of subjects. Cluster 4 pertains to mild obesity-related diabetes, most common in obese individuals, and has been identified in 18-23 percent of subjects. Cluster 5 pertains to mild age-related diabetes, especially in elderly individuals, and has been identified in 39-47 percent of subjects.

The term "diabetic neuropathy" has its usual and ordinary meaning in the medicinal arts and means peripheral neuropathy associated with diabetes mellitus in a patient. The term includes for instance diabetic neuropathies associated with microvascular injuries, irregularities in the polyols pathway, high glucose levels within cells, and or non-enzymatic glycosylation of proteins. The term contemplates among other categories: polyneuropathies, for instance, sensorimotor polyneuropathy; autonomic neuropathy; fainting upon standing up due to orthostatic hypotension; respiratory sinus arrhythmia; neuropathy affecting the gastrointestinal tract; neuropathy affecting the urinary tract; cranial neuropathies, for instance neuropathies that affect an eye and or its movement; mononeuropathies of spinal nerves; and entrapment neuropathies.

The term "symptom" as used with respect to diabetic neuropathy means a symptom thereof. Numerous such symptoms are well known in the medical arts and include but are not limited to those that arise from: microvascular injuries; irregularities in the polyols pathway; and non-enzymatic glycosylation of proteins. Non-limiting examples of symptoms of neuropathies in diabetic patients include: numbness; night-time pain which may burn, ache, or feel prickly; fainting upon standing up due to orthostatic hypotension; respiratory sinus arrhythmia; hypoglycemia; bacterial overgrowth due to reduced rate of movement through the intestines and resulting in bloat, gas and diarrhea; reflux nephropathy and other outcomes when urinary tract infections cause urinary retention; frontal pain from the eye's oculomotor nerve (e.g., third nerve palsy); effects on eyelid movement and pupil constriction; sixth-nerve effects on lateral eye movement; fourth-nerve effects on downward eye movement; spinal nerve effects that mimic the symptoms of myocardial infarction, cholecystitis, and or appendicitis; and carpal tunnel syndrome due to an entrapment neuropathy; weakness; imbalance; muscle contraction; sexual dysfunction; vision changes; impaired speech; pain and other sensations; loss of control over the bladder; and loss of control over the bowels. The term "symptom" as used with respect to diabetic neuropathy is not limited by the time over which the symptom develops, regardless of whether its appearance is sudden or over a period of years.

The term "composition" means a composition of matter, particularly for therapeutic or preventive health measures. As used with respect to treatment or prevention of pain associated with a diabetic neuropathy, the term composition means a formulation comprising one or more medicinal substances that are individually or alternatively collectively effective to alleviate the pain.

The term "topical" as used with respect to a composition has its usual and ordinary meaning in the pharmaceutical arts. In particular a topical composition is a medication applied to a body surface such as the skin or mucous membranes to treat an ailment or symptom, and particularly to alleviate or prevent pain. In particular embodiments the topical composition may be in a dose form such as a gel, solution, tincture, lotion, shake lotion, foam, cream, paste, ointment, powder, bulk solid, vapor or aerosol. In certain embodiments the topical composition is supported on a matrix such as a tape, sponge, transdermal patch, or dressing. In some embodiments the dose form is a solution for use in drops, e.g., eye drops, ear drops. In certain embodiments the dose form is in a form for application to the surface of a tooth. In a particularly preferred embodiment the topical composition has the form of a gel, but the invention is not so limited.

The term "pain" as used herein has its usual and ordinary meaning in the medical arts. The term "alleviation" as used with respect to pain means that the discomfort from the pain and or its is reduced. There are several survey-like tools to measure neuropathic pain and a drug's effectiveness in alleviating it. The Neuropathic Pain Scale is particularly well-validated. For the NPS the patient scores each of ten dimensions of pain on a scale of 1 to 10, those dimensions being: intensity; sharpness; hotness; dullness; coldness; skin sensitivity; itchiness; unpleasantness; intensity of the deep and surface pains; and duration (sporadic/intermittent, constant, or constant in the background but with flare-ups).

Summing up these items gives a 100-point scale for pain. A useful benchmark of effectiveness for the present invention is that the composition lowers the perceived diabetic neuropathic pain by 50% within a week after the onset of administration, and virtually eliminates the pain when used daily over a period of a month or more. The "virtual elimination" of pain means that the pain is essentially unnoticeable over a specific use period; it does not mean that a patient who suffers from a diabetic neuropathy remains pain-free if daily administration of the composition is halted. In certain embodiments the pain being measured is a particular pain in a particular bodily location, for instance one of: pain that feels like burning or tingling in the feet; aching hands; painful fingers; pain in legs; back pain; retinopathy; or sciatic nerve pain.

The term "pharmaceutically effective amount" as used with respect to topical compositions means that the respective composition is pharmaceutically safe and effective at the dose given.

The term "method of treatment" as used with respect to diabetic neuropathic pain contemplates therapeutic treatments as well as preventative treatments.

The terms "salts" and "esters" have their usual and ordinary meaning in organic chemistry.

The term "mixture" as used with respect to compositions means that more than one compound is present and that the multiple such compounds are mixed, whether they are medicinal compounds, excipients, and or salts and or esters of any of those.

The terms "administering" and "administration" as used with respect to applying a dose of a topical composition are not limited by the physical form of the dose or where on or in the body a dose is applied, so long as the application is topical. Typically the initial frequency of administration is four times daily although the invention is not so limited. Typically, after a break-in period of pain reduction the frequency can by reduced, and I have found that for some patients the maintenance level of administration can be as low as once daily or on an as-needed bases.

The term "solvent" has its usual and ordinary meaning in the chemical arts. The term "plurality" as used with respect to solvents in a composition means that it comprises two or more solvents. The terms "water", "dimethylsulfoxide" (DMSO), and "methylsulfonylmethane" (MSM) have their usual and ordinary meaning in the chemical arts and in particular refer respectively to $H_2O$, $(CH_3)—S(=O)—(CH_3)$, and $(CH_3)—S(=O)_2—(CH_3)$.

The term "volume percent" with respect to a chemical compound in a composition refers to the percentage of the total volume that is represented by that compound at room temperature and atmospheric pressure. Typically the volume percent is determine on the basis of the volume of the pure respective component that is provided when preparing the composition.

The term "weight percent" with respect to a chemical compound in a composition refers to the percentage of the total weight that is represented by that compound at room temperature and atmospheric pressure. Typically, the weight percent is determined on the basis of the weight of the pure respective component that is provided when preparing the composition. The terms mass and weight are used interchangeably for the purposes herein.

The term "ratio" has its usual and ordinary meaning in mathematics and statistics. The term "relative to each other" as regards the ratio of a plurality of components in a composition means that the ratio applies to some measure of each, such as by weight, weight percent, volume, volume percent, weight per volume, or some other measure.

The term "natural polyamide" means polyamides found in nature, and in particular contemplates proteins and peptides, both of which have their usual and ordinary meaning in the biochemical arts. The peptides may be as found in nature, or as synthesized, or as derived by digestion of a protein such as by use of a protease. Structural sources such as silk are particularly useful but the invention is not so limited, and for instance the invention also contemplates use of: enzymes; hormones; transport proteins; and proteins that serve other types of functions in the body. Another non-limiting example of useful proteins for purposes of the invention is glycine-rich proteins (GRPs) from plants, which serve a variety of biological functions there. For purposes of the invention a protein is defined as comprising over 50 amino acid units, and a peptide is defined as comprising from 2 to 50 amino acid units. Particularly useful peptides for the invention are those derived from cleavage of silk proteins but the invention is not so limited.

The term "amino acid" has its usual and ordinary meaning in chemistry and biochemistry with respect to proteins and peptides. The term "small amino acid" refers to an alpha-amino acid that has a relatively small residue at the alpha position. Particular small amino acids include as a hydrogen atom (glycine), methyl group (alanine), hydroxymethyl group (serine), hydroxyethyl group (threonine), or carboxymethyl group (aspartic acid). In certain embodiments the smallest amino acids are preferred, those being glycine, alanine, and serine for purposes of this invention. The invention employs natural polyamides that comprise at least 70 mole percent of the small amino acids; furthermore at least 50 mole percent of the amino acid units in those natural polyamides must be the smallest amino acids.

The term "biosynthesis" as used with respect to generation of a particular compound refers to the human body's synthesis pathway for L-carnitine. The term "characteristic of" as used with respect to that biosynthesis, means that the respective compound is part of that pathway. Compounds that are characteristic for the L-carnitine biosynthesis pathway include the following: lysine; 6-N-trimethyllysine; hydroxytrimethyllysine (HTML); 4-trimethylaminobutyraldehyde (TMABA); gamma-butyrobetaine; L-carnitine; and acetyl-L-carnitine. Compounds that are characteristic for the carnosine biosynthesis pathway include the following: cytosine; uracil; beta alanine; and carnosine.

The term "vitamin D3" has its usual and ordinary meaning in the field of nutrition. The term "metabolite of vitamin D3" means a product of human metabolism of vitamin D3. In particular vitamin D3 and metabolites thereof include cholecalciferol, calcifediol, and calcitriol.

The terms "coenzyme Q10" and "coQ10" are synonymous and refer to the family of compounds known by that name, which differ from each other in the length of the oligoisoprene tail on the quinone. With respect to coQ10 and its redox states: "fully oxidized" refers to its p-quinone form, ubiquinone; "fully reduced" refers to its p-dihydroxyphenol form, ubiquinol; and "halfoxidized" refers to its semiquinone form, ubisemiquinone. The compounds and chemical structures known by those names are well understood in the biochemical arts.

The term "purine" has its usual and ordinary meaning in biochemistry. The term "purine compound" refers to molecules that have a purine skeleton. In particular the term purine compound includes purine, adenine, adenosine, guanine, guanosine, isoguanine, inosine, hypoxanthine, xanthine, theobromine, and caffeine.

The term "purine decomposition compound" means a compound that is or can be formed by the decomposition of a purine compound, for instance by microbes or in higher organisms. Particularly preferred examples of purine decomposition compounds are uric acid and allantoin.

The term "sum of" as used with respect to compounds selected from a particular set means the aggregate when the amount of each of those selected compounds is summed up.

The term "weight percent in the aggregate" as used with respect to compounds selected from a particular set means the aggregate weight of the selected compounds expressed as a percentage relative to the weight of the whole composition in which they are present.

The terms "B vitamin", "vitamin B5", "provitamin B5", and "vitamin B6" have their usual and ordinary meaning in biochemistry.

The term "vitamin B5 compound" means a compound that is selected from the group consisting of vitamin B5, provitamin B5, and salts of vitamin B5.

The term "vitamin B6 compound" means a compound that is from the family of molecules that are both individually and collectively referred to as vitamin B6 in biochemistry. In particular, as used herein vitamin B6 compounds include: pyridoxine (PN); pyridoxine 5'-phosphate (P5P); pyridoxal (PL); pyridoxal 5'-phosphate (PLP); pyridoxamine (PM); pyridoxamine 5'-phosphate (PMP); 4-pyridoxic acid (PA), and pyritinol.

I have surprisingly discovered that topical delivery of a combination of several types of components, in certain ratios, provides outstanding pain relief for diabetic neuropathic pain. The ingredients appear to be disseminated transdermally for instance. They lower the perceived neuropathic pain by half within 7 days after the onset of administration, and virtually eliminate the pain when used daily over a longer break-in period that is typically at least a month in duration; sometimes it is longer. Although the pain returns if use is halted altogether, the level of relief from regular use substantially surpasses that of other treatments. In fact, for some patients, after the initial week or month of application with the invention compositions they are able to reduce the dosing frequency from four times daily to as little as one time daily without losing the gains in pain relief.

The composition is provided in a solvent base comprising at least water, dimethylsulfoxide (DMSO) and methylsulfonylmethane (MSM); together those solvents represent usually from 80 to 98.5 percent of the total by weight. In particular embodiments the water and DMSO together make up about 80 weight percent of the composition. Water is provided in an amount selected from one of the following ranges by weight percent relative to the whole composition: at least 45; 45 to 85; 50 to 80; 55 to 75; 60 to 70; or about 65 weight percent. DMSO is provided in an amount selected from one of the following ranges by weight percent relative to the whole composition: at least 10; 10 to 50; 15 to 45; 20 to 40; 25 to 35; or about 30%. The ratio of DMSO to MSM by weight is provided in an amount selected from one of the following ranges where the endpoints are inclusive: 4:1 to 50:1; 5:1 to 40:1; 10:1 to 30:1; 15:1 to 20:1; or 17:1 to 18:1.

Natural polyamides with high levels of small amino acid content are also provided. Typically at least 50 mole percent of the amino acids are selected from the group consisting of glycine, alanine and serine. Typically at least 70 mole percent of the amino acids are selected from the group consisting of glycine, alanine, serine, aspartic acid, and threonine. The total amount of natural polyamide is preferably selected from the following range by weight percent relative to the whole: 0.5 to 1.5; 0.5 to 1.3; 0.5 to 1.1; 0.5 to 0.9; 0.5 to 0.7; or about 0.5. Particularly good sources of these polyamides are silk proteins (e.g., fibroin) and peptides derived from silk and silk proteins. These silk sources may be mulberry or non-mulberry varieties. Mulberry silks generally have about 43% glycine units, 29% alanine units, and 10% serine units on a molar basis. Nonmulberry silks typically have about 28% glycine units, 35% alanine units, and 10% serine units on a molar basis; these also have about 5% aspartic acid units. See K. M. Babu, in Handbook of Natural Fibres: Types, Properties and Factors Affecting Breeding and Cultivation (2012), at 7.4 "Amino acid composition". Another source of proteins with small amino acid residues is the superfamily of glycine-rich proteins (GRP) in plants, which tend to be produced as a stress response and are classified in five major categories. The GRP content of glycine units is as high as 70% on a molar basis. See, e.g., M. Czolpinska and M. Rurek, "Plant Glycine-Rich Proteins in Stress Response: An Emerging, Still Prospective Story," Frontiers in Plant Science, 9:302 (2018).

One or more compounds characteristic of L-carnitine biosynthesis are provided. In particularly preferred embodiments they are provided in a range that is in the aggregate selected from one of the following, by weight percent relative to the whole composition: 0.25 to 1.0%; 0.26 to 0.90%; 0.27 to 0.80%; 0.28 to 0.70%; 0.29 to 0.60%; 0.30 to 0.50%; 0.31 to 0.40%; 0.32 to 0.35%; or about 0.33%. In various embodiments the compound selected is one or more of the following: lysine; 6-N-trimethyllysine; hydroxytrimethyllysine (HTML); 4-trimethylaminobutyraldehyde (TMABA); gamma-butyrobetaine; L-carnitine; and acetyl-L-carnitine. In a particularly preferred embodiment the compound is acetyl-L-carnitine.

One or more compounds characteristic of carnosine biosynthesis are provided. In particularly preferred embodiments they are provided in a range that is in the aggregate selected from one of the following, by weight percent relative to the whole composition: 0.15 to 2.0%; 0.20 to 1.80%; 0.25 to 1.60%; 0.30 to 1.40%; 0.35 to 1.20%; 0.40 to 1.00%; 0.40 to 0.80%; 0.45 to 0.60%; or about 0.50%. In various embodiments the compound selected is one or more of the following: cytosine; uracil; beta alanine; and carnosine. In a particularly preferred embodiment the compound is beta-alanine.

One or more compounds are provided from vitamin D3 and or vitamin D3 metabolites. In particularly preferred embodiments they are provided in a range that is in the aggregate selected from one of the following, by weight percent relative to the whole composition: 0.15 to 1.50%; 0.20 to 1.35%; 0.25 to 1.20%; 0.30 to 1.05%; 0.35 to 0.90%; 0.40 to 0.75%; 0.45 to 0.60%; or about 0.50%. In various embodiments the compound selected is one or more of the following: cholecalciferol; calcifediol; and calcitriol. In a particularly preferred embodiment the compound is cholecalciferol (vitamin D3).

One or more compounds are provided from coenzyme Q10. In particularly preferred embodiments they are provided in a range that is in the aggregate selected from one of the following, by weight percent relative to the whole composition: 0.25 to 1.50%; 0.35 to 1.35%; 0.45 to 1.20%; 0.55 to 1.05%; 0.65 to 0.90%; or about 0.75%. In various embodiments the compound selected is one or more of the following redox states: ubiquinone; ubiquinol; and semiubiquinone. In a particularly preferred embodiment the compound is ubiquinone. In various embodiments the coQ10 has an oligoisoprene tail that has a length selected from the group consisting of a monomer, dimer, trimer, tetramer, pentamer, hexamer, heptamer, octamer, nonamer, and decamer; or a combination of coQ10 compounds is provided in which the combination has a distribution of tail lengths; but the invention is not so limited. In particular embodiments coQ10 molecules are provided in which the oligoisoprene tail(s) is (are) selected from the group consisting of the hexamer, heptamer, octamer, nonamer, and decamer of isoprene.

In addition, one or more purine compounds are provided. In particularly preferred embodiments they are provided in a range that is in the aggregate selected from one of the following, by weight percent relative to the whole composition: 0.0025 to 0.25%; 0.0040 to 0.20%; 0.0055 to 0.15%; 0.0070 to 0.10%; 0.0085 to 0.05%; or about 0.010%. In various embodiments the purine compound selected is one or more of the following: purine, adenine, adenosine, guanine, guanosine, isoguanine, inosine, hypoxanthine, xanthine, theobromine, and caffeine. In particularly preferred embodiment the purine compound is caffeine.

Also, at least one purine decomposition compound is provided. In particularly preferred embodiments they are provided in a range that is in the aggregate selected from one of the following, by weight percent relative to the whole composition: 0.15 to 0.75%; 0.20 to 0.70%; 0.25 to 0.65%; 0.30 to 0.60%; 0.35 to 0.55%; 0.40 to 0.50%; or about 0.50%. In various embodiments the purine compound is one or both of uric acid and allantoin. In particularly preferred embodiment the purine compound is allantoin. In certain embodiments the purine decomposition product is provided in a weight ratio relative to the purine compound that is respectively selected from within one of the following ranges: 10:1 to 100:1; 20:1 to 85:1; 30:1 to 70:1; 40:1 to 55:1; or about 50:1. In a particular embodiment the ratio is 50:1. In a certain embodiment the ratio of compounds is 50:1 for allantoin:caffeine, respectively.

Also, at least one vitamin B5 compound is provided. In particularly preferred embodiments they are provided in a range that is in the aggregate selected from one of the following, by weight percent relative to the whole composition: 0.05 to 5.0%; 0.08 to 4.0%; 0.11 to 3.0%; 0.14 to 2.0%; 0.17 to 1.0%; or about 0.20%. In various embodiments the vitamin B5 compound selected is one or more of vitamin B5, provitamin B5 and a salt of vitamin B5. In a preferred embodiment the vitamin B5 compound is pantothenic acid (vitamin B5).

Additionally, at least one vitamin B6 compound is provided. In particularly preferred embodiments they are provided in a range that is in the aggregate selected from one of the following, by weight percent relative to the whole composition: 0.05 to 5.0%; 0.08 to 4.0%; 0.11 to 3.0%; 0.14 to 2.0%; 0.17 to 1.0%; or about 0.20%. In various embodiments the vitamin B6 compound selected is one or more of the following: pyridoxine (PN); pyridoxine 5'-phosphate (P5P); pyridoxal (PL); pyridoxal 5'-phosphate (PLP); pyridoxamine (PM); pyridoxamine 5'-phosphate (PMP); 4-pyridoxic acid (PA), and pyritinol. In a preferred embodiment the vitamin B5 compound is PLP (vitamin B6). In certain embodiments the ratio of the sum of vitamin B5 compounds to the sum of vitamin B6 compounds is selected from one of the following ranges, respectively: 30:1 to 1:30; 25:1 to 1:25; 20:1 to 1:20; 15:1 to 1:15;10:1 to 1:10; 5:1 to 1:5; 2:1 to 1:2; or about 1:1. In a certain embodiment the invention provides, relative to the whole of the composition, 0.20 weight percent pantothenic acid and 0.20 weight percent pyridoxal 5'-phosphate.

Additional excipients may optionally be included. Particular examples include Irish Moss carrageen, carbomer 940, polysorbate 80, menthol, caprylic capric triglycerides, Vitamin E as tocopheryl acetate and or mixed tocopherols, gluconolactone, sodium benzoate, modified starch, maltodextrin, benzethonium chloride, butylated hydroxytoluene, vegetable oil, and Argania Spinoza oil (Argan). Apart from Irish Moss carrageen and menthol at up to 2 weight percent each these ingredients are useful in amounts of no more than 1 weight percent each.

Table 1 provides Examples for proportions of key ingredients in compositions according to the invention.

TABLE 1

Proportions of Key Ingredients by Weight Percent

| Example # | Solvents | Natural Polyamide | L-Carnitine pathway | Carnosine pathway | D3-Related | CoQ10 | Purine-related | B vitamins |
|---|---|---|---|---|---|---|---|---|
| 1 | Water - ≥40 DMSO - ≥40 MSM - 1.75 | Mulberry Silk Peptides - 0.5 | Acetyl-L-carnitine 0.5 | Beta-alanine - 0.33 | Cholecalciferol - 0.78 | Ubiquinone - 0.75 | Allantoin - 0.50 Caffeine - 0.010 | Pantothenic Acid - 0.20 PLP - 0.20 |
| 2 | Water - ≥70 DMSO - ≥10 MSM - 2.5 | Non-mulberry Silk Peptides - 1.5 | Acetyl-L-carnitine 0.25 | Cytosine - 0.15 | Calcifediol - 0.15 | Ubiquinol - 0.25 | Allantoin - 0.25 Theobromine - 0.0025 | Pantothenic Acid - 0.05 PN - 1.5 |
| 3 | Water - ≥45 DMSO - ≥35 MSM - 0.70 | Non-mulberry Silk Protein - 1.0 | Lysine - 1.0 | Uracil - 2.0 | Calcinol - 1.5 | Ubisemiquinone - 1.5 | Uric Acid - 0.75 Xanthine - 0.075 | Panthenol 0.6 PL - 4.4 |
| 4 | Water - ≥65 DMSO - ≥15 MSM - 1.5 | Mulberry Silk Protein - 0.75 | 6-N-trimethyllysine - 0.75 | Carnosine - 0.31 | Cholecalciferol - 0.35 | Ubiquinol - 0.40 | Uric Acid - 0.30 Hypoxanthine - 0.03 | Sodium Pantothenoate - 1.2 PA - 3.8 |
| 5 | Water - ≥50 DMSO - ≥30 MSM - 0.67 | Plant GRPs - 0.25 | Hydroxyltrimethyl-lysine - 0.30 | Cytosine - 1.74 | Calcifediol - 1.3 | Ubiquinone - 1.35 | Uric Acid - 0.70 Inosine - 0.022 | Potassium Pantothenoate - 1.8 Pyritinol - 3.2 |
| 6 | Water - ≥60 DMSO - ≥20 MSM - 1.33 | Mulberry Silk Peptides - 1.3 | 4-Trimethylamino-butyraldehyde - 0.90 | Beta-alanine - 0.67 | Calcinol - 0.55 | Ubisemiquinone - 0.55 | Allantoin - 0.60 Isoguanosine - 0.06 | Panthenol - 2.4 P5P - 3.0 |
| 7 | Water - ≥55 DMSO - ≥25 MSM - 0.61 | Non-mulberry Silk Peptides - 0.7 | Gamma-butyrobetaine - 0.40 | Carnosine - 1.48 | Cholecalciferol - 1.1 | Ubisemiquinone - 1.20 | Uric Acid - 0.495 Guanosine - 0.0055 | Sodium Pantothenoate - 3.0 PM - 2.4 |
| 8 | Water - ≥67.5 DMSO - ≥12.5 MSM - 0.61 | Non-mulberry Silk Protein - 1.1 | L-carnitine - 0.80 | Uracil - 0.93 | Calcifediol - 0.75 | Ubiquinone - 0.70 | Allantoin - 0.35 Guanine - 0.010 | Pantothenic Acid - 3.6 PL - 1.8 |
| 9 | Water - ≥42.5 DMSO - ≥37.5 MSM - 1.2 | Mulberry Silk Protein - 0.9 | Acetyl-L-carnitine - 0.60 | Beta-alanine - 1.22 | Calcinol - 0.9 | Ubiquinol - 1.05 | Uric Acid - 0.175 Adenosine - 0.0025 | Potassium Pantothenoate - 4.2 PL - 1.2 |
| 10 | Water - ≥57.5 DMSO - ≥22.5 MSM - 0.9 | Plant GRPs - 0.5 | L-carnitine - 0.70 | Carnosine - 0.35 | Cholecalciferol - 0.7 | Ubiquinone - 0.90 | Allantoin - 0.90 Adenine - 0.015 | Pantothenic Acid - 4.8 PLP - 0.6 |
| 11 | Water - ≥52.5 DMSO - ≥27.5 MSM - 0.92 | Plant GRPs - 0.3 | L-carnitine - 0.50 | Carnosine - 0.25 | Cholecalciferol - 0.5 | Ubiquinone - 0.85 | Allantoin - 0.15 Purine - 0.015 | Panthenol - 5.0 PMP - 0.16 |

Example 12A—Preparation of Unscented Gel

A gel was prepared using the proportions from Table 1, Example 1, by weight percent for water, DMSO, beta-alanine, MSM, ubiquinone, silk peptides, allantoin, caffeine, vitamin D3, vitamin B5, vitamin B6, and acetyl-L-carnitine; the specific amounts of water and DMSO were 47.5 and 40.5 weight percent respectively. The composition further contained the following excipients in amounts of no more than 2 weight percent each: Irish moss carrageen; Carbomer® 940; caprylic capric triglycerides; tocopheryl acetate; mixed tocopherols; gluconolactone, sodium benzoate, modified starch, maltodextrin, butylated hydroxytoluene, vegetable oil, and Argania spinozo oil (argan).

Example 12B—Method of Use of Unscented Gel

The composition was applied over the entire areas of discomfort 3-4 times per day for the first 7-10 days, and thereafter on an as-needed basis. It was massaged until completely absorbed into skin.

Example 13A—Preparation of Scented Solution

A solution was prepared using the proportions from Table 1, Example 1, by weight percent for water, DMSO, beta-alanine, MSM, ubiquinone, silk peptides, allantoin, caffeine, vitamin D3, vitamin B5, vitamin B6, and acetyl-L-carnitine; the specific amounts of water and DMSO were 48 and 40.45 weight percent respectively. The composition further contained 2 weight percent menthol and the following excipients in amounts of no more than 1 weight percent each: polysorbate 80; caprylic capric triglycerides; tocopheryl acetate; mixed tocopherols; gluconolactone, sodium benzoate, benzethonium chloride, modified starch, maltodextrin, butylated hydroxytoluene, vegetable oil, and Argania spinozo oil (argan).

Example 13B—Use of Scented Solution

The solution was sprayed upon skin over the entire areas of discomfort 3-4 times per day for the first 7-10 days, and thereafter on an as-needed basis. No massaging was needed to work the solution into the skin. Due to irritation from menthol the gel was not applied upon mucous areas.

Alternatively the solution was rolled upon skin over the entire areas of discomfort 3-4 times per day for the first 7-10 days, and thereafter on an as-needed basis. No massaging was needed to work the solution into the skin. Due to irritation from menthol the gel was not applied upon mucous areas.

As the following Examples show, in general, at least halving of the pain symptoms is to be expected over a break-in period of one week, with sustained benefits thereafter as long as the dosing with the composition continues to be maintained. Over longer periods of use the pain is further reduced from the level achieved in the initial break-in period. In addition, other neuropathic symptoms, such as stiffness, numbness, and or seeming paralysis of some body parts, have also been observed to be reduced by administration of the invention compositions, and to flare up again when the administration is halted.

Example 14—Patient No. 1

A Type 2 diabetic Caucasian female, in her 70s, was suffering from neuropathic pain in her feet whenever she was not standing; she also suffered from tight tendons in the back of her legs. This condition had continued unabated for the recent several years despite being under the routine care of physicians, moreover sleeping with a prescribed splint had failed to provide relief. By applying the gel according to Examples 12A and 12B she was able to obtain relief from the pain rapidly for a duration of several hours. Following this relief, by ongoing usage of the composition she continued experiencing the same benefits during a 2-month follow-up period.

Example 15—Patient No. 2

A Type 2 diabetic Caucasian male, in his 50s, was suffering from neuropathic pain in his feet that felt as if they were on fire, to the point that it took him 20 minutes to dress himself. He also suffered from tightness in his knees and legs. By applying the gel according to Examples 12A and 12B within a week he was able to obtain rapid relief from most of the pain for a duration of several hours. In addition, his stiffness was abated. Following this relief, by ongoing usage of the composition she continued experiencing the same benefits during a 3-month follow-up period.

Example 16—Patient No. 3

A Type 2 diabetic Asian male, aged 36, was suffering from documented chronic neuropathic back pain for which he had been prescribed muscle relaxers and Percocet®, but without substantial pain relief. Over the course of applying the gel according to Examples 12A and 12B for a period of a month, on a 10-point scale his pain fell from a 6 to a 1. He also experienced an improved range of motion with less pain. Following this relief he was able to fall back to applying the composition first thing in the morning, and continued experiencing the same benefits during a 6-month follow-up period.

Example 17—Patient No. 4

A Type 2 diabetic African American male, in his 40s, was suffering from neuropathic pain, from drop foot, also from legs that did not seem to wake up when the rest of his body did. By applying the gel according to Examples 12A and 12B he was able to obtain rapid relief, including also increased sensitivity to touch and temperature in numb areas. Following this relief, by ongoing daily usage of the composition he continued experiencing the same benefits during a 5-month follow-up period.

Example 18—Patient No. 5

A Type 2 diabetic Caucasian female, in her early 60s, was suffering from crippling neuropathic pain leg cramps, to the point that she could barely walk. By applying the gel according to Examples 12A and 12B within a week she was able to obtain rapid relief from the cramps and most of the pain in her legs and feet. Following this relief, by ongoing usage of the composition she continued experiencing the same benefits during a 2-week follow-up period.

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A method for alleviating pain from a diabetic neuropathy by topical administration to a patient in need thereof a pharmaceutically effective amount of a composition consisting of:
   a) a plurality of solvents consisting of a combination of water, dimethylsulfoxide (DMSO) and methylsulfonylmethane (MSM), wherein:
      i) the composition is at least 45 volume percent water;
      ii) the composition is at least 10 volume percent DMSO; and
      iii) the ratio of DMSO:MSM is between 4:1 and 50:1, inclusive;
   b) at least one natural polyamide selected from the group consisting of proteins and peptides, wherein the natural polyamide is selected from the group consisting of a mulberry silk protein, a peptide derived from a mulberry silk protein, a nonmulberry silk protein, a peptide derived from a non-mulberry silk protein, a glycine-rich protein from a plant, and a peptide derived from a glycine-rich protein (GRP) from a plant:
   c) at least one compound characteristic of L-carnitine biosynthesis, wherein the compound is selected from the group consisting of: lysine, 6-N-trimethyllysine; hydroxytrimethyllysine (HTML), 4-trimethylaminobutyraldehyde (TMABA), gamma-butyrobetaine, L-carnitine, and acetyl-L-carnitine;
   d) at least one compound characteristic of carnosine biosynthesis, wherein the compound is selected from the group consisting of: cytosine, uracil, beta alanine, and carnosine;
   e) at least one compound selected from the group consisting of vitamin D3 and vitamin D3 metabolites, wherein the group consists of: cholecalciferol, calcifediol, and calcitriol;
   f) coenzyme Q10 (coQ10), wherein the coQ10 is present in one or more redox states selected from the group consisting of: fully oxidized (ubiquinone), semiquinone (ubisemiquinone), and fully reduced (ubiquinol);
   g) at least two compounds selected from the group consisting of purine compounds and purine decomposition compounds, wherein:
      i) at least one compound is a purine compound selected from the group consisting of purine, adenine, adenosine, guanine, guanosine, isoguanine, inosine, hypoxanthine, xanthine, theobromine, and caffeine;
      ii) at least one compound is a purine decomposition compound selected from the group consisting of uric acid and allantoin; and
      iii) the ratio of purine decomposition compound(s): purine compound(s) is between 10:1 and 100:1, inclusive;
   h) two B vitamins selected from the group consisting of:
      i) a B5 compound selected from the group consisting of vitamin B5, provitamin B5 and salts of vitamin B5;
      ii) a vitamin B6 compound; and
      iii) the ratio of the B5 compound:vitamin B6 compound is between 1:30 and 30:1, inclusive; and
   i) the topical composition having:
      i) 0.5 to 1.5 weight percent in the aggregate of the at least one natural polyamide;
      ii) 0.25 to 1.0 weight percent in the aggregate of the at least one compound characteristic of L-carnitine biosynthesis;
      iii) 0.15 to 2.0 weight percent in the aggregate of the at least one compound characteristic of carnosine biosynthesis;
      iv) 0.15 to 1.5 weight percent in the aggregate of the at least one compound selected from the group consisting of vitamin D3 and vitamin D3 metabolites;
      v) 0.25 to 1.5 weight percent in the aggregate of the coQ10 that is present in one or more redox states;
      vi) 0.15 to 0.75 weight percent in the aggregate of the at least one purine decomposition compound(s);
      vii) 0.0025 to 0.25 weight percent in the aggregate of the at least one purine compound(s);
      viii) 0.05 to 5.0 weight percent in the aggregate of the B5 compound(s); and
      ix) 0.05 to 5.0 weight percent in the aggregate of the vitamin B6 compound(s);
   j) Irish Moss carrageen, and
   k) optionally polysorbate 80, caprylic capric triglycerides, tocopheryl acetate, mixed tocopherols, gluconolactone, sodium benzoate, benzethonium chloride, modified starch, maltodextrin, butylated hydroxytoluene, vegetable oil, menthol, and Argania spinozo oil,
      wherein the only vitamins in the composition are a B5 compound, a vitamin B6 compound, vitamin D3 or a vitamin D3 metabolite, and optionally vitamin E.

2. The method of claim 1, wherein the composition is in a form selected from the group consisting of a gel and a solution.

3. The method of claim 1, wherein the composition is supported on a matrix selected from the group consisting of tapes, sponges, transdermal patches, and dressings.

4. The method of claim 1, wherein the diabetic neuropathic pain is measured by the Neuropathic Pain Scale.

5. The method of claim 1, wherein the neuropathic pain is associated with diabetes that is selected from the group consisting of gestational diabetes, type 1 diabetes, type 2 diabetes, Cluster 2 diabetes, Cluster 3 diabetes, Cluster 4 diabetes, and Cluster 5 diabetes.

6. The method of claim 1, wherein the diabetic neuropathic pain is associated with a condition selected from the group consisting of microvascular injuries, non-enzymatic glycosylation of proteins, polyneuropathies, autonomic neuropathy, fainting upon standing up due to orthostatic hypotension, respiratory sinus arrhythmia, neuropathy affecting the gastrointestinal tract, neuropathy affecting the urinary tract, cranial neuropathies, mononeuropathies of spinal nerves, and entrapment neuropathies.

7. The method of claim 1, wherein the diabetic neuropathic pain is a symptom that appeared gradually over a period of years.

8. The method of claim 1, wherein the topical administration is by application to a body surface selected from the group consisting of skin, and mucous membranes.

9. The method of claim 1, wherein the natural polyamide is selected from the group consisting of mulberry silk proteins, nonmulberry silk proteins, and glycine-rich proteins from plants.

10. The method of claim 1, wherein the composition consists of:
    a) from 45 to 85 weight percent water;
    b) from 10 to 50 weight percent DMSO;
    c) 1.75 weight percent MSM;
    d) 0.5 weight percent of the natural polyamide, wherein the polyamide consists of peptides derived from silk proteins;
    e) 0.33 weight percent beta-alanine;
    f) 0.5 weight percent acetyl-L-carnitine;

g) 0.75 weight percent cholecalciferol (vitamin D3);
h) 0.75 weight percent ubiquinone;
i) 0.5 weight percent allantoin;
j) 0.01 weight percent caffeine;
k) 0.20 weight percent pantothenic acid (vitamin B5);
l) 0.20 weight percent pyridoxal phosphate; and
m) less than or equal to 2 weight percent Irish Moss carrageen.

11. The method of claim 1, wherein the composition reduces diabetic neuropathic pain by 50% within 3 to 5 days after administration of the composition.

12. The method of claim 1, wherein the composition eliminates diabetic neuropathic pain when the composition is administered over a period of at least one month.

13. The method of claim 1, wherein the composition is administered three or four times daily for an initial period of from one week to one month.

14. The method of claim 13, wherein the composition is administered one time daily after the initial period.

15. The method of claim 13, wherein the composition is administered on an as-needed basis after the initial period.

16. The method of claim 1, wherein the composition is a gel and wherein the gel is applied topically over an entire area of discomfort.

17. The method of claim 1, wherein the composition is a solution and wherein the solution is sprayed topically over an entire area of discomfort.

18. The method of claim 1, wherein the composition is a solution and wherein the solution is rolled upon skin over an entire area of discomfort.

* * * * *